United States Patent [19]

Clark et al.

[11] Patent Number: 4,947,839

[45] Date of Patent: Aug. 14, 1990

[54] ORTHOPEDIC CASTING MATERIAL HAVING REDUCED TACK AND REDUCED SLIP

[75] Inventors: James L. Clark; Ali Ozsahin, both of Tulsa, Okla.

[73] Assignee: Carapace, Tulsa, Okla.

[21] Appl. No.: 233,597

[22] Filed: Aug. 18, 1988

[51] Int. Cl.$^5$ .............................................. A61F 5/04
[52] U.S. Cl. .................................. 128/90; 128/89 R; 523/105; 427/2
[58] Field of Search ............... 128/89 R, 90; 428/241, 428/290; 427/2; 523/105, 111

[56] References Cited

U.S. PATENT DOCUMENTS

| | | | |
|---|---|---|---|
| 3,043,298 | 7/1962 | Brickman et al. | 128/91 |
| 3,089,486 | 5/1963 | Pike | 128/90 |
| 3,630,194 | 12/1971 | Boardman | 128/90 |
| 3,763,858 | 10/1973 | Buese | 128/156 |
| 4,169,469 | 10/1979 | Arluck | 128/90 |
| 4,411,262 | 10/1983 | von Bonin et al. | 128/90 |
| 4,454,873 | 6/1984 | Laufenberg et al. | 128/90 |
| 4,502,479 | 3/1985 | Garwood et al. | 128/90 |
| 4,643,909 | 2/1987 | Kammerer | 128/90 |
| 4,655,202 | 4/1987 | Potter et al. | 128/90 |
| 4,667,661 | 5/1987 | Scholz et al. | 128/90 |
| 4,672,956 | 6/1987 | Potter et al. | 128/90 |
| 4,690,842 | 9/1987 | Kammerer et al. | 128/90 |

*Primary Examiner*—Randall L. Green
*Assistant Examiner*—Paul Prebilic
*Attorney, Agent, or Firm*—Woodcock Washburn Kurtz Mackiewicz & Norris

[57] ABSTRACT

An orthopedic casting material comprising a fabric impregnated and/or coated with a reactive fluid polyisocyanate prepolymer which hardens when wetted with water is treated with a mixture of oil and polymeric micro-powder to produce a material with reduced tack, reduced slip and reduced foaming properties compared to similar commercially available products. The material is further preferably coated or impregnated with a filler such as amorphous silicate.

7 Claims, No Drawings

ORTHOPEDIC CASTING MATERIAL HAVING REDUCED TACK AND REDUCED SLIP

BACKGROUND OF THE INVENTION

This invention relates to an orthopedic casting material. More specifically, the invention relates to such casting materials which comprise fabric impregnated and/or coated with polyisocyanate prepolymer and which are treated with mineral oil and fluorocarbon polymer powder to reduce the tack, slip and foaming properties of the material during curing.

Most orthopedic casting tapes currently available are produced using curable resins coated on a substrate such as fiberglass, polyester or other synthetic or natural fabrics. For example, orthopedic casting tapes utilizing polyisocyanate prepolymers which react with water to initiate curing to polyurethanes are known. (U.S. No. 4,411,262 to von Bonin et al., U.S. No. 4,502,479 to Garwood et al.) Generally, the polyisocyanate prepolymer comprises the reaction product of an isocyanate and a polyol, which product polymerizes to polyurethane upon contact with water. The prepolymer-treated bandage is soaked in water prior to application to the body member, and the wet bandage is then applied to the body member. After the bandage is applied, the cast is smoothed with a gloved hand and held at certain points until it hardens. Since the resins in the bandage are quite tacky until they cure, the protective gloves worn by the cast applier tend to stick to the bandage. This is disadvantageous since it can lead to unwinding of the cast as layers of the tape pull apart from each other and the cast cannot be molded.

To alleviate the problem of "tackiness" in curable resin-coated bandages, Scholz et al. proposed, in U.S. No. 4,667,661, treating such bandages with certain lubricants to reduce the kinetic coefficient of friction of such sheets to less than about 1.2. The lubricant can be comprised of (a) hydrophilic groups which are covalently bonded to the curable resin, (b) an additive which is incompatible with the curable resin or (c) a combination of (a) and (b). As noted in the Scholz et al. patent (e.g., column 11, lines 21 et. seq.), the bandages treated with such lubricants become very slippery, and molding of the cast becomes easy due to the non-tacky nature of the resin. It is also noted in the Scholz et al. patent (column 8, lines 45-65) that materials such as mineral oil were evaluated as lubricants and, although they did give a non-tacky and even slippery feeling to the surface of the casting tape, which allowed easy application and moldability of the tape to the patient, the effect was transient. On average, Scholz et al. report, such materials lasted only a day to a week, apparently due to the dissolution of the oil into the resin.

It is believed that products embodying the Scholz et al. invention are now commercially available. Users often complain that such bandages, while certainly not possessing the degree of tackiness associated with other prior bandages, are actually too slippery for easy handling and application.

Another problem common with polyurethane prepolymer resin coated or impregnated sheets is foaming of the resin. Foaming occurs when carbon dioxide is released upon reaction of water with isocyanate groups in the resin. Foaming is undesirable since it reduces the porosity of the cast and its overall strength. It has been suggested (U.S. No. 4,667,661) to reduce foaming by adding foam suppressors such as silicone Antifoam A (Dow Corning), DB-100 silicone fluid (Dow corning) to the resin, but the use of very hydrophilic additives to obtain tack-free casting tapes, such as the hydrophilic additives proposed by Scholz et al., exacerbates the foaming problem in the cast.

There therefore exists a need for a bandage material with improved handling properties, i.e., one which is neither too tacky nor too slippery, and with a reduced tendency to foam compred to commercially available products.

SUMMARY OF THE INVENTION

It has now been found that such bandages can be obtained by coating or impregnating a water-curable resin sheet with a mixture of oil and polymeric micro-powder. This invention, therefore, relates to an orthopedic casting material comprising a fabric impregnated and/or coated with a combination of a reactive fluid polyisocyanate prepolymer which hardens when said resin is wetted with water and a mixture of an oil which is immiscible with said prepolymer and polymeric micro-powder. Preferably, the sheets are also coated or impregnated with a small amount of a high volume, low density inorganic filler material. The bandage materials of this invention have the advantage of being easily handled, i.e., they are neither too tacky nor too slippery. An added advantage of the treated sheets of this invention is that, upon curing and hardening, the sheets have a very smooth surface which is aesthetically appealing and over which items of clothing may easily slide.

DETAILED DESCRIPTION OF THE INVENTION

The types of fabric upon which a curable polyisocyanate prepolymer is coated or in which such prepolymer may be impregnated have been well described in the art. (E.g., U.S. No. 4,667,661 and U.S. No. 4,411,262, the disclosures of which are herein incorporated by reference.) The sheet is semi-rigid or flexible and should be porous so that the curing agent, water, may penetrate into the roll of fabric and contact all parts of the resin. Examples of suitable sheets are woven, non-woven or knit fabrics comprised of natural or synthetic fibers. Preferred sheets are knit fiberglass fabrics, although fabrics of cotton and polyester, for example, may also be used.

The polyisocyanate prepolymer used in this invention comprises a prepolymer derived from polyisocyanate, preferably aromatic, and a reactive hydrogen compound or oligomer. The preferred prepolymer composition comprises modified diphenylmethane diisocyanate, polypropylene glycol, benzoyl chloride stabilizer and dimorpholinodiethylether catalyst. The preferred isocyanate to diol ratio is about 4 to 1 (NCO/OH=4/1). To prolong the shelf life of the material, certain stabilizers such as benzoyl chloride (0.1 to 1.0 wt.%) may be included in the prepolymer, and foam suppressors such as silicone liquids may also be included.

The amount of prepolymer applied to the fabric must be sufficient for the formation of a strong interlayer laminate bond but not so much as to occlude the porosity and unnecessarily thicken the resin film which should be thin for rapid and complete hardening. Excessive prepolymer may cause the fabric to be messy to handle because of stickiness or dripping and transfer of resin. The desired resin to carrier fabric weight ratio is a function of both the prepolymer viscosity and the surface characteristics of the fabric and is therefore not susceptible to precise quantification; however, an appropriate ratio could be easily determined by one skilled in the art.

The advantageous non-tacky yet non-slippery properties of the casting materials of this invention are achieved by coating and/or incorporating into the casting material a "detackifier" mixture comprising an oil which is immiscible with the prepolymer and a polymeric micro-powder. It is believed that the powder serves to immobilize the mineral oil on the surface of the casting material, so that it is neither released to produce a greasy-feeling product nor migrates away from the surface so that it is unavailable to reduce the tackiness of the curing resin. It is further believed that the presence of the polymeric micro-powders contribute to the smooth surface of the cured cast.

Mineral oil is the preferred oil for use in this invention because it is inert, non-toxic, stable and homogeneous and because it has no objectional odors; however, oils such as soybean oil, corn oil, peanut oil, safflower oil, oliver oil, sunflower oil and vegetable oil may also be used.

The micropowders used in this invention preferably have an average particle size of no more than about 10 microns, more preferably no more than about 1 micron. Fluorocarbon polymer powders are most preferred because they are inert, stable and non-toxic. Fluorocarbon polymer powders are available with average particle sizes as great as 50 microns; however, the higher the particle size, the smaller the total surface area of the powders, and, thus, the more likely it is that the powder will separate from the oil, resulting in less efficient immobilization of the oil. Best results have been achieved using a fluorocarbon powder with an average particle size of less than about 1 micron. Other polymeric micropowders can be used in place of or in combination with fluorocarbon polymer powders. The polyolefins, especially polyethylene micropowders, are examples of other suitable micropowders. Examples of commercially available polymeric micropowders which are suitable for use in this invention include Slyp-Ayd Micronized Powder Polyolefin Blend, Daniel Products Co., Jersey City, NJ, a dry, micronized powder of a composition of halogenated polyolefins, polyethylenes and other synthetic waxes; and Telfon DLX-6000 Industrial Fluoropolymer, E. I. du Pont de Nemours and Co., Wilmington, DE.

In the preferred embodiment of this invention, a high volume, low density inorganic filler material, such as an amorphous silicate powder, is also incorporated into the casting material. Tests indicate that the presence of a small amount (e.g., up to about 30 weight %, preferably about 10 weight %, based on the detackifier mixture) of such a filler material decreases the set time and improves the compressive strength of the cast. The inorganic filler preferably has an average particle size in the range of about 25 to 30 microns. Although other inorganic fillers such as mica might be used, amorphous silicates such as Dicaperl (Grefco, Inc., Torrance, CA) are preferred because of their bubble shape (hollow sphere) and very low bulk density. Fumed silicas are also preferred materials. The filler material may be mixed in with the oil and polymeric micro-powder and applied to the casting material as described below. Alternatively, one might blend the amorphous silicate in with the polyisocyanate prepolymer, apply the prepolymer to the fabric, followed by coating with the oil/powder mixture.

Generally speaking, the detackifier mixture will comprise 2–40% (by weight) of the polymeric micro-powder, 60–98% oil, and 0–30% inorganic filler. Best results have been achieved using a combination of 80 weight % mineral oil, 10 weight % fluorocarbon polymer powder, and 10 weight % amorphous silicate. The oil and polymeric micro-powder are preferably combined with high sheer prior to application to the cast material. The mixture may then either be applied to the surface of the cast material, such as by coating or spraying, or may be impregnated in the material, such as by being combined with the polyisocyanate prepolymer prior to its application to the fabric.

When the mineral oil/powder mixture is applied as a coating, it is preferably applied in the amount of about 2 to about 10%, based on the weight of prepolymer. Below about 2%, there is not enough of the mixture to provide the desired non-tack, non-slip properties, and above about 10%, the product is too oily. Best results have been obtained, in surface coating or spraying, using about 4 to 5% of the oil/powder mixture, based on the weight of prepolymer. The mixture may be applied as a continuous surface coating or may be applied in a discontinuous pattern such as in stripes. When the mineral oil/powder mixture is impregnated into the material, such as by being combined with the polyisocyanate prepolymer, more of the mixture is required to achieve the same tack-free characteristics. Generally, about 10 to 20% of the mixture, based on weight of prepolymer, is suitable for this form of application; however, the presence of the mixture in the polyisocyanate prepolymer can be disadvantageous in that it tends to slow down the curing reaction.

The materials of this invention are further illustrated by the following examples, which are intended to be illustrative and not limiting of the scope of this invention.

EXAMPLES 1–8

Bound Lubricants

EXAMPLE 1

Two 3.8 liter (one gallon) glass reaction vessels each equipped with a 12.7 cm×2.54 cm×0.318 cm (5×1×⅛") Teflon(TM) impeller, addition funnel, nitrogen purge line, thermometer, and vacuum pump inlet line were assembled and purged for a period of 30 minutes to ensure the entire apparatus was completely dry. The reaction vessels are marked "A" and "B."

Resin Premix A

The following chemicals were added to reactor "A" in order at 10 minute intervals:

| CHEMICALS | Wt. (g) | Wt. % |
|---|---|---|
| Isonate 143L (Upjohn Co.)[1] | 293.0 | 58.6 |
| SAG-47 (Union Carbide)[2] | 1.0 | 0.2 |
| Benzoyl Chloride (Velsicol Chem.) | 0.5 | 0.1 |

[1]diphenylmethane diisocyanate
[2]silicone antifoam agent

While agitating the vessel was placed under a vacuum of approximately −1 atmosphere and dried for a period of 1 hour.

The vacuum was removed along with the agitator, thermometer, and addition funnel. The vessel was sealed.

Resin Premix B

The following chemicals were added to reactor "B" in order at 10 minute intervals:

| CHEMICALS | Wt. (g) | Wt. % |
|---|---|---|
| Pluracol P 710 (BASF)[1] | 195.5 | 39.1 |
| DMDEE (Texaco Chemical)[2] | 10.0 | 2.0 |

[1] polypropylene glycol
[2] dimorpholinodiethylether

The agitation rate was gradually increased as the viscosity increased. The vessel was placed under a vacuum of approximately −1 atmosphere and dried for a period of 4 hours.

The vacuum was removed along with the agitator, thermometer, and addition funnel. The vessel was sealed.

Resin: Addition of Premix "B" to Premix "A"

Both vessels were placed under a continuous nitrogen purge and the contents of vessel "B" were added to the contents of vessel "A" at the rate of approximately 10.5 grams per minute. The temperature of the vessel was allowed to increase to 55° C. The vessel was purged continuously with nitrogen and agitated for a period of 1 and a half hours.

DETACKIFIER

A 3.8 liter (one gallon) glass vessel equipped with 12.7 cm×2.54 cm×0.318 cm (5×1×⅛") Teflon(TM) impeller, addition funnel, and nitrogen purge line was assembled and purged for a period of 30 minutes to ensure the entire apparatus was completely dry. The following chemicals were added to the reactor through the addition funnel in order and at 5 minute intervals:

| CHEMICALS | Wt. (g) | Wt. % |
|---|---|---|
| Drakeol 35 (Penreco)[1] | 80.0 | 80.0 |
| DLX6000 (Du Pont)[2] | 10.0 | 10.0 |
| Dicaperl HP220[3] | 10.0 | 10.0 |

[1] mineral oil
[2] fluorocarbon micropowder
[3] amorphous silicate

The agitation rate was gradually increased as the viscosity increased. The vessel was then sealed.

The contents of the vessel were added to the contents of vessel "A" while under a continuous nitrogen purge. Vessel "A" was agitated for a period of 1 hour.

The resin was coated onto three inch wide Raschel Knit fiberglass scrim composed of 100% Owens-Corning ECDE 75 1/0 0.7Z TPI Natural color fiberglass, continuous yarn (front and back bar). The resin & detackifier coating was 48.5% by weight. The fabric was converted into rolls 3.66 m (12 feet) in length. These rolls were packaged individually into moisture proof pouches.

60.96 cm (24") samples were tested at one and ten days according to the modified ASTM D 1894 as disclosed in U.S. Pat. No. 4,667,661, issued May 26, 1987. The samples tested after one day were found to have a mean kinetic coefficient of friction of 1.06. The samples tested at ten days were found to have a mean kinetic coefficient of friction of 1.06 as well.

This material was also tested for handling characteristics by a panel of six orthopaedic technicians. Prior to wrapping the experimental rolls each member of the panel was asked to wrap several rolls of 3M's Scotchcast Plus, Johnson & Johnson's Delta-Lite 'S,' and Kirschner's K-Cast. The panel was asked to compare the experimental materials with the commercially available products mentioned above. Each member was asked to provide comparative comments.

Each member of the panel opened the pouch, removed the roll (while wearing vinyl surgical gloves), and immediately immersed the roll in 23.9° C. water for 3 seconds. The roll was given a firm squeeze while immersed to aid in distribution of the water to the tape. The roll was then removed from the water and squeezed lightly to remove excess water. Each panel member wrapped the roll around a 2" stainless steel mandrel to form a cylinder approximately 8" in length. Each panel member evaluated the handling characteristics of the roll, to include: unwind of the roll, moldability, water-loss, foaming, and finished appearance.

The handling characteristics of this material were judged to be very good. Panel members stated that the product did not foam and water-loss/dripping was much less than 3M's Scotchcast Plus and Johnson & Johnson's Delta-Lite S.

EXAMPLE 2

The following resin and detackifier were prepared, mixed, coated, and packaged according to Example 1:

| CHEMICALS | Wt. (g) | Wt. % |
|---|---|---|
| Drakeol 35 (Penreco) | 60.0 | 80.0 |
| Acumist(TM) B-6 (Allied Signal)[1] | 7.5 | 10.0 |
| Dicaperl HP220 | 7.5 | 10.0 |

[1] micronized polyethylene wax

This material was tested according to the KCOF method and exhibited a mean kinetic coefficient of friction of 1.1 at one day and 1.09 at ten days.

The handling characteristics of this material were judged to be very good. No foaming and very clean/no mess as compared to the above-mentioned 3M and Johnson & Johnson products.

EXAMPLE 3

The following resin and detackifier were prepared, mixed, coated, and packaged according to Example 1:

| CHEMICALS | Wt. (g) | Wt. % |
|---|---|---|
| Soybean Oil | 80.0 | 80.0 |
| DLX6000 | 10.0 | 10.0 |
| Dicaperl HP220 | 10.0 | 10.0 |

This material was tested according to the KCOF method and exhibited a mean kinetic coefficient of friction of 1.08 at one day and 1.09 at ten days.

The handling characteristics of this material were judged to be very good. No foaming and very clean/no mess as compared to the 3M and Johnson & Johnson products.

EXAMPLE 4

The following resin and detackifier were prepared, mixed, coated, and packaged according to Example 1:

| CHEMICALS | Wt. (g) | Wt. % |
| --- | --- | --- |
| Corn Oil | 40.0 | 80.0 |
| Acumist( TM ) B-6 | 5.0 | 10.0 |
| Dicaperl HP520 | 5.0 | 10.0 |

This material was tested according to the KCOF method and exhibited a mean kinetic coefficient of friction of 1.32 at one day and 1.32 at ten days.

The members of the test panel considered this material fair. It was felt that the material was too dry or tacky. Considerable resistance to molding was evident. No foaming and very clean/no mess as compared to the 3M and Johnson & Johnson products.

EXAMPLE 5

The following resin and detackifier were prepared, mixed, coated, and packaged according to Example 1:

| CHEMICALS | Wt. (g) | Wt. % |
| --- | --- | --- |
| Peanut Oil | 89.0 | 80.0 |
| Acumist( TM ) B-6 | 10.0 | 10.0 |
| Cab-o-sil[1] | 1.0 | 1.0 |

[1]fumed silica

This material was tested according to the KCOF method and exhibited a mean kinetic coefficient of friction of 1.22 at one day and 1.22 at ten days.

This material was judged to possess excellent handling characteristics, superior to other products currently on the market.

EXAMPLE 6

The following resin and detackifier were prepared, mixed, coated, and packaged according to Example 1:

| CHEMICALS | Wt. (g) | Wt. % |
| --- | --- | --- |
| Safflower Oil | 60.0 | 80.0 |
| DLX6000 | 7.5 | 10.0 |
| Dicaperl HP220 | 7.5 | 10.0 |

This material was tested according to the KCOF method and exhibited a mean kinetic coefficient of friction of 1.24 at one day and 1.25 at ten days.

This material was judged to possess excellent handling characteristics, superior to other products currently on the market.

EXAMPLE 7

The following resin and detackifier were prepared, mixed, coated, and packaged according to Example 1:

| CHEMICALS | Wt. (g) | Wt. % |
| --- | --- | --- |
| Olive Oil | 40.0 | 80.0 |
| DLX6000 | 5.0 | 10.0 |
| Aerosil R972[1] | 0.25 | 0.5 |

[1]fumed silica

This material was tested according to the KCOF method and exhibited a mean kinetic coefficient of friction of 1.30 at one day and 1.29 at ten days.

The members of the test panel considered this material very good, but very close to being too dry or tacky.

EXAMPLE 8

The following resin and detackifier were prepared, mixed, coated, and packaged according to Example 1:

| CHEMICALS | Wt. (g) | Wt. % |
| --- | --- | --- |
| Sunflower Oil | 80.0 | 80.0 |
| Acumist( TM ) B-6 | 10.0 | 10.0 |
| Dicaperl HP220 | 10.0 | 10.0 |

This material was tested according to the KCOF method and exhibited a mean kinetic coefficient of friction of 1.1 at one day and 1.11 at ten days.

This material was qualified as possessing very good handling characteristics.

EXAMPLES 9-18

Surfactant Lubricants

EXAMPLE 9

A 3.8 liter (one gallon) glass vessel equipped with 12.7 cm×2.54 cm×0.318 cm (5×1×⅛") Teflon(* TM ) impeller, addition funnel, and nitrogen purge line was assembled and purged for a period of 30 minutes to ensure the entire apparatus was completely dry. The following chemicals were added to the reactor through the addition funnel in order and at 5 minute intervals:

| CHEMICALS | Wt. (g) | Wt. % |
| --- | --- | --- |
| Drakeol 35 (Penreco) | 480.0 | 80.0 |
| DLX6000 | 60.0 | 10.0 |
| Dicaperl HP220 | 60.0 | 10.0 |

The agitation rate was gradually increased as the viscosity increased.

The detackifier was coated onto three inch wide resin impregnated fiberglass scrim having a resin content of 48.5% by weight. A grooved transfer roller system was used to apply the detackifier in stripes running the length of the substrate. The stripes were ⅛" wide in ⅛" intervals. This method is preferable to a complete surface coat. This method minimizes the amount of detackifier that must be added to the substrate without sacrificing handling characteristics.

The coated fabric was converted to individual rolls 3.66 m (12 feet) in length. The addition of the detackifier to the roll resulted in a 5.2% increase in the weight of the roll. These coated rolls were packaged individually into moisture proof pouches. Ten days after coating 5 rolls were then tested according to the modified ASTM D 1894 as disclosed in U.S. Pat. No. 4,667,661, issued May 26, 1987. The samples were found to have a mean kinetic coefficient of friction of 1.28 after one day and 1.28 after ten days.

This material was judged to possess very good handling characteristics by the panel of orthopaedic technicians.

EXAMPLE 10

The following detackifier was prepared, applied, and packaged according to the procedure of Example 9:

| CHEMICALS | Wt. (g) | Wt. % |
| --- | --- | --- |
| Drakeol 35 | 480.0 | 80.0 |
| Slip-Ayd - SL 600[1] | 60.0 | 10.0 |
| Dicaperl HP220 | 60.0 | 10.0 |

[1]micronized powder polyolefin blend

This material was tested according to the KCOF method and exhibited a mean kinetic coefficient of friction of 1.25.

This material was judged to possess excellent handling characteristics by the panel of orthopaedic technicians.

EXAMPLE 11

The detackifier was prepared, applied, and the material packaged according to Example 9:

| CHEMICALS | Wt. (g) | Wt. % |
| --- | --- | --- |
| Soybean Oil | 480.0 | 80.0 |
| DLX6000 | 60.0 | 10.0 |
| Dicaperl HP220 | 60.0 | 10.0 |

This material was tested according to the KCOF method and exhibited a mean kinetic coefficient of friction of 1.22 at one day and 1.23 at ten days.

The handling characteristics of this material were judged to be excellent.

EXAMPLE 12

The following detackifier was prepared according to Example 1. A grooved transfer roller was used to apply the detackifier in ⅛" stripes (running the length of the tape) at 3/16" intervals. The material was packaged according to Example 1:

| CHEMICALS | Wt. (g) | Wt. % |
| --- | --- | --- |
| Corn Oil | 480.0 | 80.0 |
| Acumist(TM) B-6 | 60.0 | 10.0 |
| Dicaperl HP520 | 60.0 | 10.0 |

This material was tested according to the KCOF method and exhibited a mean kinetic coefficient of friction of 1.57 at one day and 1.58 at ten days.

The members of the test panel considered this material poor. It was felt that the material was too dry or tacky. Considerable resistance to molding was evident.

It was noted by the panel that this material was less tacky and more acceptable than Kirschner's K-Cast.

EXAMPLE 13

The following detackifier was prepared, applied, and packaged according to Example 9:

| CHEMICALS | Wt. (g) | Wt. % |
| --- | --- | --- |
| Peanut Oil | 537.0 | 89.5 |
| Acumist(TM) B-6 | 60.0 | 10.0 |
| Cab-o-sil | 3.0 | 0.5 |

This material was tested according to the KCOF method and exhibited a mean kinetic coefficient of friction of 1.17 at one day and 1.17 at ten days.

This material was judged to possess excellent handling characteristics.

EXAMPLE 14

The following detackifier was prepared, applied, and packaged according to Example 9:

| CHEMICALS | Wt. (g) | Wt. % |
| --- | --- | --- |
| Safflower Oil | 480.0 | 80.0 |
| DLX6000 | 60.0 | 10.0 |
| Dicaperl HP220 | 60.0 | 10.0 |

This material was tested according to the KCOF method and exhibited a mean kinetic coefficient of friction of 1.28 at one day and 1.29 at ten days.

This material was judged to possess very good handling characteristics.

EXAMPLE 15

The following detackifier was prepared, applied, and packaged according to Example 9:

| CHEMICALS | Wt. (g) | Wt. % |
| --- | --- | --- |
| Olive Oil | 534.0 | 89.0 |
| DLX6000 | 60.0 | 10.0 |
| Aerosil R972 | 6.0 | 1.0 |

This material was tested according to the KCOF method and exhibited a mean kinetic coefficient of friction of 1.35 at one day and 1.35 at ten days.

The members of the test panel considered this material good, but almost too dry or tacky.

EXAMPLE 16

The following detackifier was prepared, applied, and packaged according to Example 9:

| CHEMICALS | Wt. (g) | Wt. % |
| --- | --- | --- |
| Sunflower Oil | 480.0 | 80.0 |
| Acumist(TM) B-6 | 60.0 | 10.0 |
| Dicaperl HP820 | 60.0 | 10.0 |

This material was tested according to the KCOF method and exhibited a mean kinetic coefficient of friction of 1.1 at one day and 1.11 at ten days.

This material was qualified as possessing very good handling characteristics.

EXAMPLE 17

The following detackifier was prepared, applied, and packaged according to Example 9:

| CHEMICALS | Wt. (g) | Wt. % |
| --- | --- | --- |
| Drakeol 35 | 480.0 | 80.0 |
| Acumist(TM) B-6 | 120.0 | 10.0 |

This material was tested according to the KCOF method and exhibited a mean kinetic coefficient of friction of 0.51 at one day and 0.62 at ten days.

This material was judged to be too slippery and not as manageable or dry as previous examples. Panel members stated that this material was nearly equivalent to that of 3M's Scotchcast Plus and Johnson & Johnson's Delta-Lite 'S' in handling. This material was judged to be fair. Panel members found the roll difficult to hold while wrapping and pulling the tape (the tape was pulled to simulate techniques used to conform the tape to a patient's limb).

EXAMPLE 18

Untreated Casting Tape

Resin prepared and coated according to Example 1 was tested according to the KCOF method and exhibited a mean kinetic coefficient of friction of 2.56 at one day and 2.56 at ten days.

This material was judged to be very difficult to work with. The technicians disliked the material due to its extreme tackiness.

What is claimed is:

1. An orthopedic casting material comprising a fabric coated or impregnated with a combination of a reactive fluid polyisocyanate prepolymer which hardens when said resin is wetted with water and detackifier mixture comprising an oil which is immiscible with said prepolymer and polymeric micro-powder, said polymeric micropowder comprising a fluorocarbon polymer powder having an average particle size of no more than about 1 micron.

2. The casting material of claim 1 in which said oil is mineral oil.

3. The casting material of claim 1 in which said polyisocyanate prepolymer comprises the reaction product of diphenylmethane diisocyanate and polypropylene glycol.

4. The casting material of claim 3 in which said oil is mineral oil.

5. The casting material of claim 1 which further comprises a high volume, low density inorganic filler material.

6. The casting material of claim 5 in which said detackifier mixture comprises about 2–40 wt.% polymeric micropowder, about 60–98 wt.% oil and 0–30 wt.% inorganic filler material, based on total weight of said detackifier mixture, and in which said inorganic filler has an average particle size of about 25 to 30 microns.

7. The casting material of claim 5 in which said filler material is selected from the group consisting of amorphous silicates and fumed silica.

* * * * *